United States Patent
Dhuper et al.

(10) Patent No.: US 10,052,451 B2
(45) Date of Patent: Aug. 21, 2018

(54) GAS DELIVERY VENTURI

(71) Applicant: AEON RESEARCH AND TECHNOLOGY, INC., Hewlett, NY (US)

(72) Inventors: Sunil Kumar Dhuper, Old Westbury, NY (US); Greg Marler, Rockford, IL (US)

(73) Assignee: AEON RESEARCH AND TECHNOLOGY, INC., Hewlett, NY (US)

( * ) Notice: Subject to any disclaimer, the term of this patent is extended or adjusted under 35 U.S.C. 154(b) by 225 days.

(21) Appl. No.: 15/015,733

(22) Filed: Feb. 4, 2016

(65) Prior Publication Data

US 2016/0220778 A1 Aug. 4, 2016

Related U.S. Application Data

(62) Division of application No. 13/748,305, filed on Jan. 23, 2013, now Pat. No. 9,289,568.

(Continued)

(51) Int. Cl.
 *A61M 16/12* (2006.01)
 *A61M 16/08* (2006.01)
 (Continued)

(52) U.S. Cl.
 CPC .......... *A61M 16/208* (2013.01); *A61M 11/00* (2013.01); *A61M 11/04* (2013.01);
 (Continued)

(58) Field of Classification Search
 CPC ............ A61M 16/1005; A61M 16/127; A61M 2016/1025; A61M 2202/0208;
 (Continued)

(56) References Cited

U.S. PATENT DOCUMENTS 1,640,528 A * 8/1927 Bruhn ................. B01F 15/0266
222/478
2,796,295 A 6/1957 McKinnon
(Continued)

FOREIGN PATENT DOCUMENTS

GB 869626 A * 5/1961 .......... B05B 7/0416
RU 2009113454 11/2010
SU 175623 1/1966

*Primary Examiner* — Jackie Tan-Uyen T Ho
*Assistant Examiner* — Joseph D Boecker
(74) *Attorney, Agent, or Firm* — Leason Ellis LLP

(57) ABSTRACT

A venturi connector includes a housing having a mixing chamber defined therein and at least one window that is in fluid communication with the mixing chamber and is open to atmosphere to allow air to be entrained into the mixing chamber. The connector includes a nozzle actuator member includes a body having a plurality of discrete nozzles formed therein. The nozzles are defined by different sized venturi orifices through which gas flows, thereby allowing the concentration of the gas delivered to the patient to be varied. The nozzle actuator member is disposed within one window formed in the housing between the gas port and the mixing chamber such that the position of the nozzle actuator member within the housing can be adjusted so as to position one of the discrete nozzles into the gas flow path, thereby controlling the flow rate of the gas into the mixing chamber and ultimately the concentration of gas delivered to the patient.

18 Claims, 10 Drawing Sheets

Related U.S. Application Data

(60) Provisional application No. 61/694,020, filed on Aug. 28, 2012, provisional application No. 61/610,828, filed on Mar. 14, 2012, provisional application No. 61/589,671, filed on Jan. 23, 2012.

(51) Int. Cl.
*A61M 16/10* (2006.01)
*A61M 16/20* (2006.01)
*A61M 16/06* (2006.01)
*A61M 16/00* (2006.01)
*A61M 11/04* (2006.01)
*A61M 15/00* (2006.01)
*A61M 11/00* (2006.01)
*A61M 16/14* (2006.01)

(52) U.S. Cl.
CPC ...... *A61M 15/009* (2013.01); *A61M 15/0065* (2013.01); *A61M 15/0086* (2013.01); *A61M 16/0057* (2013.01); *A61M 16/06* (2013.01); *A61M 16/0816* (2013.01); *A61M 16/0833* (2014.02); *A61M 16/0875* (2013.01); *A61M 16/1005* (2014.02); *A61M 16/1045* (2013.01); *A61M 16/12* (2013.01); *A61M 16/127* (2014.02); *A61M 16/20* (2013.01); *A61M 16/209* (2014.02); *A61M 16/0078* (2013.01); *A61M 16/14* (2013.01); *A61M 2202/0208* (2013.01)

(58) Field of Classification Search
CPC ...... A61M 2205/12; A61M 2205/3334; A61M 16/0003; A61M 16/0012; A61M 16/0057; A61M 16/08; A61M 16/0816; A61M 16/0875; A61M 16/10; A61M 16/122; A61M 16/125; B01F 5/042; B01F 2005/0435; B01F 2005/044; B05B 1/1636; B05B 1/1645; B05B 1/1654; B05B 1/169
USPC ........... 128/203.25, 204.24, 204.25, 205.11, 128/205.24; 239/390–392, 394, 396
See application file for complete search history.

(56) References Cited

U.S. PATENT DOCUMENTS

| | | |
|---|---|---|
| D184,636 S | 3/1959 | Pickerell et al. |
| 2,906,265 A | 9/1959 | Samuels |
| 2,990,563 A | 7/1961 | Davidson |
| 3,057,347 A | 10/1962 | McGee |
| 3,104,062 A | 9/1963 | Mahon |
| D198,964 S | 8/1964 | Dash et al. |
| 3,184,115 A | 5/1965 | Meshberg |
| D206,979 S | 2/1967 | Jaffe |
| D207,143 S | 3/1967 | Goodwin |
| 3,666,955 A | 5/1972 | Suprenant et al. |
| 3,714,944 A | 2/1973 | Price |
| 3,826,413 A | 7/1974 | Warren |
| 3,850,171 A * | 11/1974 | Ball ............ A61M 16/06 128/204.25 |
| D233,845 S | 12/1974 | Fettel et al. |
| 3,903,884 A | 9/1975 | Huston et al. |
| 3,977,432 A | 8/1976 | Vidal |
| 4,036,253 A | 7/1977 | Fegan |
| 4,043,511 A * | 8/1977 | Nakamura ............ B05B 1/083 239/394 |
| 4,114,811 A | 9/1978 | Loeffler |
| D251,203 S | 2/1979 | Williamson |
| 4,190,046 A | 2/1980 | Virag |
| 4,210,155 A | 7/1980 | Grimes |
| D258,535 S | 3/1981 | Reichl |
| 4,291,688 A | 9/1981 | Kistler |
| D262,320 S | 12/1981 | Mono |
| D264,940 S | 6/1982 | Stock |
| D272,094 S | 1/1984 | Wolf et al. |
| 4,463,755 A | 8/1984 | Suzuki |
| 4,470,412 A | 9/1984 | Nowacki et al. |
| 4,554,916 A | 11/1985 | Watt |
| 4,584,998 A | 4/1986 | McGrail |
| 4,637,528 A | 1/1987 | Wachinski et al. |
| 4,641,644 A | 2/1987 | Andersson et al. |
| 4,648,628 A | 3/1987 | Meadows et al. |
| 4,649,912 A | 3/1987 | Collins |
| 4,669,463 A | 6/1987 | McConnell |
| 4,711,378 A | 12/1987 | Anderson |
| D294,175 S | 2/1988 | Briggs |
| 4,739,756 A | 4/1988 | Horn |
| 4,821,714 A | 4/1989 | Smelser |
| 4,823,784 A | 4/1989 | Bordoni et al. |
| 4,830,224 A | 5/1989 | Brison |
| 4,848,333 A | 7/1989 | Waite |
| 4,850,371 A | 7/1989 | Broadhurst et al. |
| D304,232 S | 10/1989 | Fuller |
| 4,886,055 A | 12/1989 | Hoppough |
| 4,903,897 A * | 2/1990 | Hayes ............ B05B 1/1654 239/394 |
| D307,183 S | 4/1990 | Kalayjian |
| D308,576 S | 6/1990 | Iversen |
| 4,951,661 A | 8/1990 | Sladek |
| 4,953,545 A | 9/1990 | McCarty |
| 5,012,803 A | 5/1991 | Foley et al. |
| 5,020,530 A | 6/1991 | Miller |
| 5,039,134 A | 8/1991 | Meadow et al. |
| 5,078,131 A | 1/1992 | Foley |
| 5,099,833 A | 3/1992 | Michaels |
| 5,119,809 A | 6/1992 | Gerson |
| D328,244 S | 7/1992 | Hamilton et al. |
| 5,146,916 A | 9/1992 | Catalani |
| 5,146,936 A | 9/1992 | Ng |
| D335,175 S | 4/1993 | Sladek |
| 5,231,983 A | 8/1993 | Matson et al. |
| 5,263,485 A | 11/1993 | Hickey |
| 5,277,175 A | 1/1994 | Riggs et al. |
| 5,287,849 A | 2/1994 | Piper et al. |
| 5,349,946 A | 9/1994 | McComb |
| 5,357,946 A | 10/1994 | Kee et al. |
| 5,372,129 A * | 12/1994 | Ryder ............ A61M 16/12 128/204.25 |
| 5,385,140 A | 1/1995 | Smith |
| 5,386,940 A * | 2/1995 | Berfield ............ B05B 1/1654 239/394 |
| 5,388,571 A | 2/1995 | Roberts et al. |
| 5,438,982 A | 8/1995 | MacIntyre |
| 5,479,920 A | 1/1996 | Piper et al. |
| 5,482,031 A | 1/1996 | Lambert |
| 5,504,224 A | 4/1996 | Wilson |
| 5,513,630 A | 5/1996 | Century |
| 5,542,412 A | 8/1996 | Century |
| 5,546,930 A | 8/1996 | Wikefeldt |
| 5,570,686 A | 11/1996 | Century |
| 5,579,758 A | 12/1996 | Century |
| 5,586,551 A | 12/1996 | Hilliard |
| 5,588,424 A | 12/1996 | Insler et al. |
| 5,594,987 A | 1/1997 | Century |
| 5,606,789 A | 3/1997 | Century |
| 5,613,489 A | 3/1997 | Miller et al. |
| 5,617,844 A | 4/1997 | King |
| 5,628,305 A | 5/1997 | Melker |
| 5,640,951 A | 6/1997 | Huddart et al. |
| 5,642,730 A | 7/1997 | Baran |
| 5,701,886 A | 12/1997 | Ryatt |
| 5,727,542 A | 3/1998 | King |
| 5,738,087 A | 4/1998 | King |
| 5,752,502 A | 5/1998 | King |
| 5,791,340 A | 8/1998 | Schleufe et al. |
| 5,813,423 A | 9/1998 | Kirchgeorg |
| 5,816,240 A | 10/1998 | Komesaroff |
| 5,848,587 A | 12/1998 | King |
| 5,848,588 A | 12/1998 | Foley et al. |
| 5,862,543 A * | 1/1999 | Reynoso ............ A61H 33/027 239/394 |

(56) References Cited

U.S. PATENT DOCUMENTS

| | | |
|---|---|---|
| 5,865,172 A | 2/1999 | Butler et al. |
| 5,964,223 A | 10/1999 | Baran |
| 5,988,162 A | 11/1999 | Retallick, III |
| 6,039,042 A | 3/2000 | Sladek |
| 6,041,777 A | 3/2000 | Faithfull et al. |
| 6,078,730 A | 6/2000 | Huddart et al. |
| 6,079,413 A | 6/2000 | Baran |
| 6,116,233 A | 9/2000 | Denyer et al. |
| 6,192,884 B1 | 2/2001 | Vann et al. |
| 6,340,023 B2 | 1/2002 | Elkins |
| 6,363,932 B1 | 4/2002 | Forchione et al. |
| 6,390,090 B1 | 5/2002 | Piper |
| 6,427,685 B1 | 8/2002 | Ray |
| 6,450,163 B1 | 9/2002 | Blacker et al. |
| 6,494,202 B2 | 12/2002 | Farmer |
| 6,550,476 B1 | 4/2003 | Ryder |
| 6,584,969 B2 | 7/2003 | Farmer |
| 6,609,518 B2 | 8/2003 | Lamb |
| 6,612,308 B2 | 9/2003 | Stenzler et al. |
| 6,622,725 B1 | 9/2003 | Fisher et al. |
| 6,679,252 B2 | 1/2004 | Sladek |
| 6,705,316 B2 | 3/2004 | Blythe et al. |
| 6,748,945 B2 | 6/2004 | Grychowski et al. |
| 6,772,754 B1 | 8/2004 | Mendenhall |
| 6,776,160 B2 | 8/2004 | Wang |
| 6,799,423 B2 | 10/2004 | Piekarski |
| 6,929,003 B2 | 8/2005 | Blacker et al. |
| 6,976,488 B2 | 12/2005 | Halperin |
| 6,994,083 B2 | 2/2006 | Foley et al. |
| 7,036,500 B2 | 5/2006 | Niles et al. |
| 7,080,643 B2 | 7/2006 | Grychowski et al. |
| 7,131,439 B2 | 11/2006 | Blacker et al. |
| 7,191,776 B2 | 3/2007 | Niles et al. |
| 7,204,245 B2 | 4/2007 | Johnson et al. |
| 7,290,541 B2 | 11/2007 | Ivri et al. |
| 7,353,811 B2 | 4/2008 | Weisz |
| 7,360,541 B2 | 4/2008 | Dhuper et al. |
| 7,445,006 B2 | 11/2008 | Dhuper et al. |
| 7,493,898 B2 | 2/2009 | King |
| 7,743,764 B2 | 6/2010 | Dhuper et al. |
| 7,841,341 B2 | 11/2010 | Dhuper et al. |
| 7,841,342 B2 | 11/2010 | Dhuper et al. |
| 7,861,713 B2 | 1/2011 | Dhuper et al. |
| 7,870,857 B2 | 1/2011 | Dhuper et al. |
| 7,926,484 B2 | 4/2011 | Dhuper et al. |
| 8,074,649 B2 | 12/2011 | Dhuper et al. |
| 8,181,646 B2 | 5/2012 | Dhuper et al. |
| 8,534,280 B2 | 9/2013 | Dhuper et al. |
| 8,616,200 B2 | 12/2013 | McKinnon et al. |
| 2002/0017302 A1 | 2/2002 | Fukunaga et al. |
| 2002/0069870 A1 | 6/2002 | Farmer |
| 2002/0092928 A1* | 7/2002 | Conroy ............... B05B 1/1654 239/392 |
| 2002/0121275 A1 | 9/2002 | Johnson et al. |
| 2002/0129814 A1 | 9/2002 | Sladek |
| 2003/0010336 A1 | 1/2003 | Vito |
| 2003/0209246 A1 | 11/2003 | Schroeder et al. |
| 2004/0011364 A1 | 1/2004 | Dhuper et al. |
| 2004/0024372 A1 | 2/2004 | Grogan |
| 2004/0060560 A1 | 4/2004 | Stenzler et al. |
| 2004/0084048 A1 | 5/2004 | Stenzler et al. |
| 2004/0123974 A1 | 7/2004 | Marler et al. |
| 2004/0226563 A1 | 11/2004 | Xu et al. |
| 2004/0234610 A1 | 11/2004 | Hall et al. |
| 2005/0028811 A1 | 2/2005 | Nelson et al. |
| 2005/0039747 A1 | 2/2005 | Fukunaga et al. |
| 2005/0092325 A1 | 5/2005 | Dionne |
| 2005/0092329 A1 | 5/2005 | Sta-Maria |
| 2005/0247313 A1 | 11/2005 | Niles et al. |
| 2006/0231090 A1 | 10/2006 | King |
| 2006/0231091 A1 | 10/2006 | Camarillo |
| 2006/0237559 A1* | 10/2006 | Chih ............... B05B 1/1654 239/394 |
| 2006/0249158 A1 | 11/2006 | Dhuper et al. |
| 2006/0260607 A1 | 11/2006 | Dhuper et al. |
| 2007/0062531 A1 | 3/2007 | Fisher et al. |
| 2007/0068516 A1 | 3/2007 | Dhuper et al. |
| 2007/0137644 A1 | 6/2007 | Dhuper et al. |
| 2008/0087280 A1 | 4/2008 | Dhuper et al. |
| 2009/0173348 A1 | 7/2009 | Fisher et al. |
| 2010/0032500 A1* | 2/2010 | Righini ............... B05B 1/1654 239/393 |
| 2010/0071693 A1 | 3/2010 | Allum et al. |
| 2010/0294254 A1 | 11/2010 | Ward |
| 2011/0277754 A1 | 11/2011 | Mckinnon et al. |
| 2012/0097170 A1 | 4/2012 | Dawson |
| 2012/0240924 A1* | 9/2012 | Rustad ............... A61M 16/12 128/203.12 |
| 2012/0312898 A1* | 12/2012 | Sesser ............... A01G 25/16 239/394 |
| 2013/0192597 A1 | 8/2013 | McKinnon et al. |

\* cited by examiner

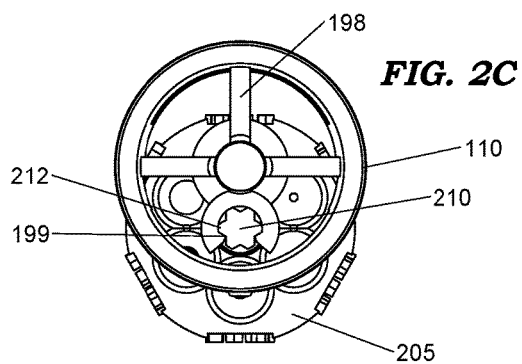
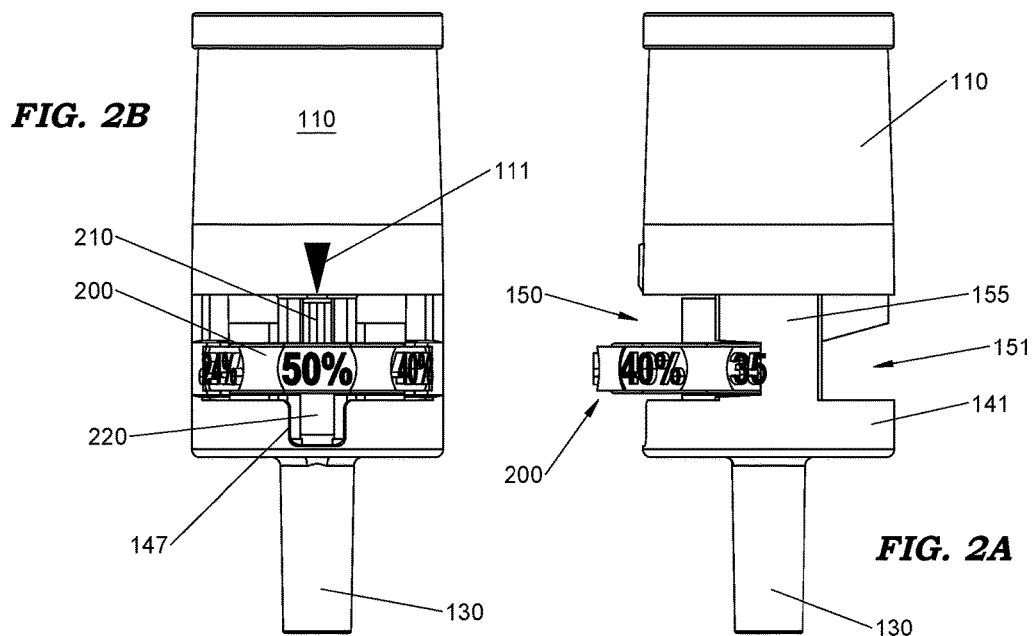
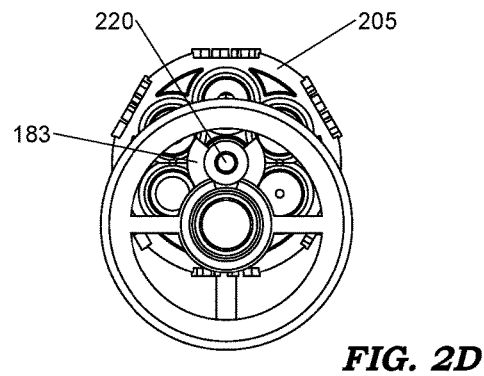

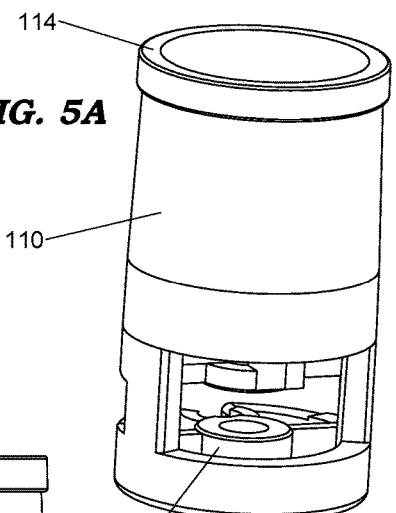
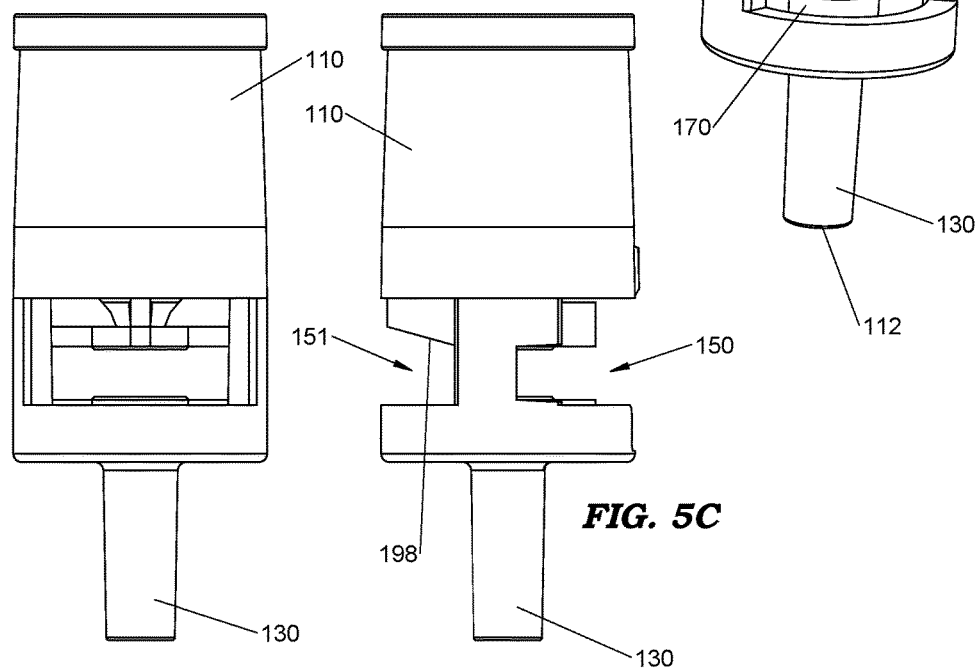
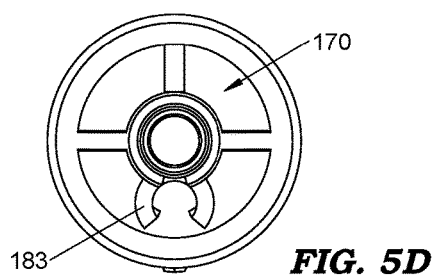
FIG. 5A
FIG. 5B
FIG. 5C
FIG. 5D

SECTION A-A

GAS DELIVERY VENTURI

CROSS-REFERENCE TO RELATED APPLICATIONS

The present application is a divisional of U.S. patent application Ser. No. 13/748,305, filed Jan. 23, 2013, which claims the benefit of: U.S. patent application Ser. No. 61/589,671, filed on Jan. 23, 2012; U.S. patent application No. 61/610,828, filed Mar. 14, 2012 and U.S. patent application No. 61/694,020, filed Aug. 28, 2012, each of which is hereby incorporated by reference in its entirety.

BACKGROUND

The venturi effect is the reduction in fluid pressure that results when a fluid flows through a constricted section of pipe. Many hospital patients require a supplementary level of oxygen in the room air they are breathing, rather than pure or near pure oxygen and this can be delivered through a number of devices dependant on the diagnoses, clinical condition of a patient, level of blood oxygenation (hypoxemia), flow requirement and in some instances patient preference. There are also a number of devices available for oxygen delivery in a spontaneously breathing patient, some of the options being low flow nasal cannula, high flow nasal cannula, face mask, venturi mask, non-rebreather mask, oxygen tent, CPAP/BIPAP mask, etc. The venturi mask is especially desirable where highly controlled low concentration is required, especially in patients who are sensitive to high concentration oxygen and are at a risk of carbon dioxide retention when given high concentration oxygen (an example of such patient would be one with the diagnoses of COPD).

The venturi mask, also known as an air-entrainment mask, is a medical device to deliver a known oxygen concentration to patients on controlled oxygen therapy. Venturi devices often use flow rates between 2 and 12 LPM, with a concentration of oxygen delivered to the patient of between 24% and 50%. Venturi masks are considered high-flow oxygen therapy devices. This is because venturi masks are able to provide total inspiratory flow at a specified $F_iO_2$ (fraction of inspired oxygen) to a patient's therapy. The kits usually include multiple jets in order to set the desired $F_iO_2$ which are usually color coded. The color of the device reflects the delivered oxygen concentration, for example: blue=24%; yellow=28%; white=31%; green=35%; pink=40%; orange=50%. The color however varies with different brands and the user must check the instructions for use to determine the correct color for the desired $F_iO_2$. A venturi connector can be used and is connected to the patent through a face mask or the like and to a gas source (in this case oxygen) which delivers oxygen to the patient by means of the face mask. The venturi connector has air entrainment openings or ports that draw air into the connector for mixing with the gas (oxygen) that is flowing through the venturi connector to deliver a metered amount of a gas mixture to the patient.

Though venturi masks may accurately deliver a predetermined oxygen concentration to the trachea, generally up to 50%, there could be a greater level of inaccuracy in delivering higher concentration when a patient's flow requirement is high during respiratory distress and a high level of air entrainment happens through the secondary entrainment ports that are mostly a part of the interface mask device. There may be a reasonable level of predictability when considering primary air entrainment from the primary venturi entrainment ports but there is high level of unpredictability when considering the secondary entrainment from the interface mask device entrainment ports. Hence, a patient could be at a risk of developing hypoxemia due to inaccurately delivered low oxygen concentration than stated or predicted. The current venturi devices are therefore fraught with problems and need improvement and better accuracy or predictability.

There are other disadvantages with a venturi system, and that is that there are a large number of parts that are included in the venturi kit, especially multiple venturi connectors and therefore, the kit can be rather bulky and cumbersome. For example, if the oxygen concentration has to be varied, a completely new venturi connector having the proper jet (nozzle) is needed and thus, requires the previous nozzle to be removed and then the new nozzle is connected to the rest of the equipment. In addition, the flow of oxygen has to be adjusted for each venturi connector. This task requires time and moreover, is an interruption to the patient's treatment. In addition, most medical providers other than respiratory therapists are not easily familiar with the intricacies of venturi devices, they are not familiar with venturi principals, they require special training, and as such the devices currently being used are not user friendly. The parts of the kit that are not used, thus must be carefully stored and kept track of and could easily get misplaced which is not common in a hospital setting.

There is therefore a need for an improved venturi gas delivery system.

SUMMARY

A venturi connector includes a housing having a mixing chamber defined therein and at least one window that is in fluid communication with the mixing chamber and is open to atmosphere to allow air to be entrained into the mixing chamber. The venturi connector also includes a gas port extending outwardly from the housing for connecting to a gas source. The gas port defines a gas flow path for delivering the gas to the mixing chamber. In addition, a nozzle actuator member includes a body having a plurality of discrete nozzles formed therein. The nozzles are defined by different sized venturi orifices through which gas flows, thereby allowing the concentration of the gas delivered to the patient to be varied. The nozzle actuator member is disposed within one window formed in the housing between the gas port and the mixing chamber such that the position of the nozzle actuator member within the housing can be adjusted so as to position one of the discrete nozzles into the gas flow path, thereby controlling the flow rate of the gas into the mixing chamber and the gas concentration delivered to the patient.

BRIEF DESCRIPTION OF THE DRAWING FIGURES

FIGS. 1A-B show a gas delivery venturi connector according to one exemplary embodiment of the present invention;

FIG. 2A is a side elevation view of the gas delivery venturi connector of FIG. 1;

FIG. 2B is a side elevation view of the gas delivery venturi connector of FIG. 1;

FIG. 2C is a top plan view of the gas delivery venturi connector of FIG. 1;

FIG. 2D is a bottom plan view of the gas delivery venturi connector of FIG. 1;

FIG. 5A is a side perspective view of the gas delivery venturi connector body of FIG. 1;

FIG. 5B is a side elevation view of the gas delivery venturi connector body of FIG. 1;

FIG. 5C is a side elevation view of the gas delivery venturi connector body of FIG. 1;

FIG. 5D is a bottom perspective view of the gas delivery venturi connector body of FIG. 1;

DETAILED DESCRIPTION OF CERTAIN EMBODIMENTS

Figures 1A, 1B:
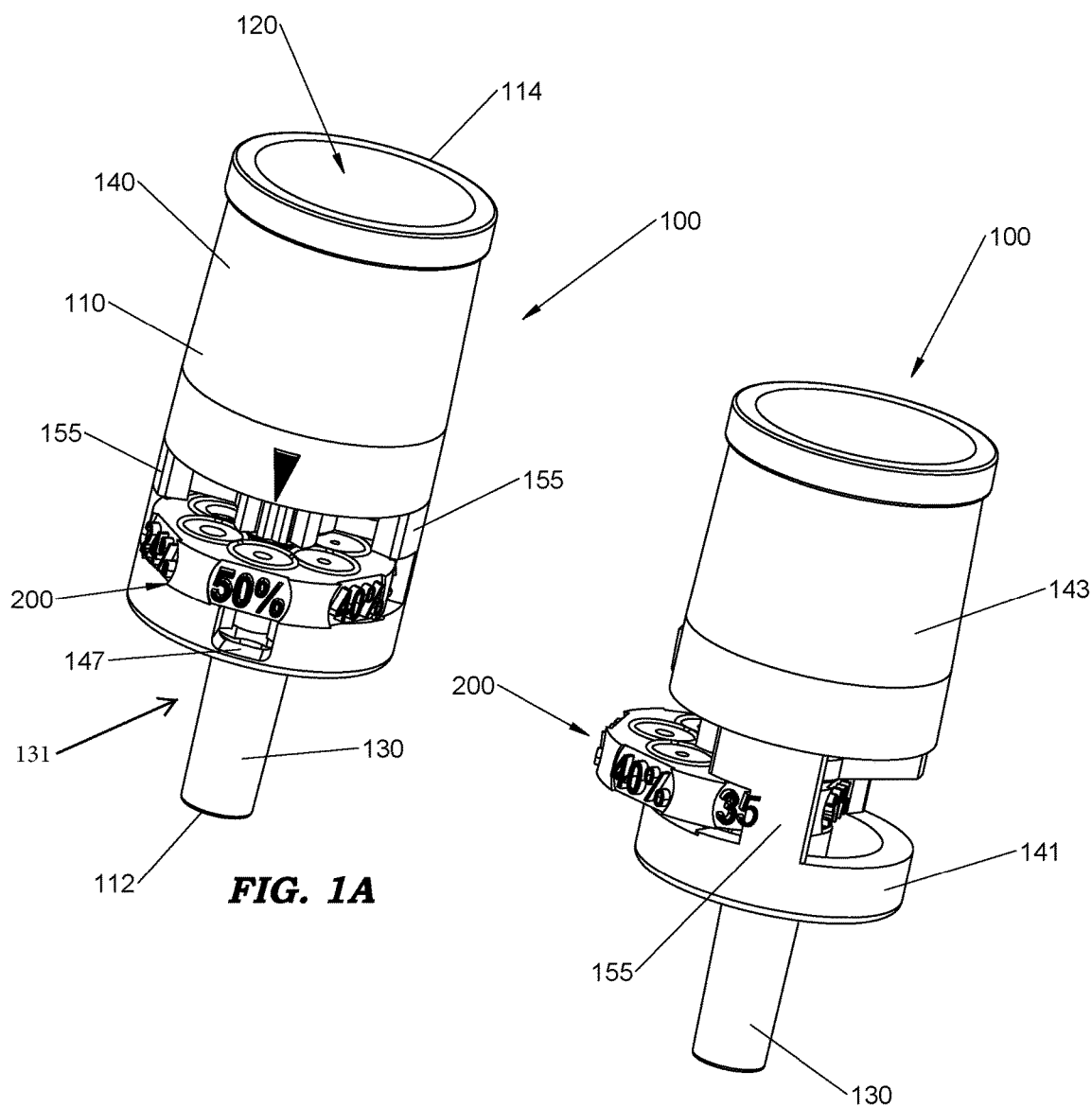

FIGS. 1A-B illustrate a venturi connector 100 according to one embodiment for use in a venturi gas delivery system.

As described above, a venturi gas delivery system includes a patient interface/face mask and the venturi (connector, etc.) that includes a jet (nozzle) having a specific gas flow rate to provide a total inspiratory flow at a specified $F_iO_2$ for patient therapy. The connector 100 is formed of two distinct parts, namely, a venturi connector body or housing 110 and an adjustable actuator member 200 that permits the user to choose from among a plurality of different inspiratory oxygen concentrations depending upon the precise application and the patient's needs. As described herein, the actuator member 200 is received within but is movable relative to the housing 110 to allow the user to effectively select (e.g., dial in) the desired inspiratory oxygen concentration delivered to the patient.

In accordance with the present invention, the venturi connector 100 is constructed to be attached to a gas source (not shown), such as an oxygen gas source, and is also connected to a face mask (not shown) or the like that delivers the inhalation gas to the patient.

The venturi connector 100 includes the connector body or housing 110 that has a first end 112 and an opposing second end 114. The first end 112 is the end of the housing 110 that is connected to the gas source, while the second end 114 is connected via a conduit member to the face mask. The housing 110 is a substantially hollow structure and thus fluid can flow therethrough. The housing 110 thus has an inner cavity or chamber 120 that is open at the second end 114.

As shown in FIGS. 1-5, the housing 110 generally has two distinct sections, namely a first section 131 that terminates at the first end 112 and a second section 140 that terminates at the second end 114. The first section 131 is in the form of a gas port that can be an elongated tube through which gas from the gas source can flow into the second section 140 of the housing 110. As described herein, the second section 140 is the portion of the housing 110 in which air is entrained into the flow of the gas (from the gas source) to form a gas mixture that is delivered to the patient. The inner cavity 120 is located within the second section 140.

The second section 140 includes one or more air entrainment windows 150, 151. The air entrainment window 150 is an opening (slot) formed in the housing 110 at a location that allows air to freely flow into the inner cavity 120 where is mixed with the gas that is delivered into the housing 110 via the gas port 130. In the illustrated embodiment, the air entrainment window 150 is in the form of an arcuate shaped window formed in the housing 110. The window 150 has a width (W) and a height (H). As explained below, the window 150 is generally located between the inner cavity 120 (mixing chamber) and the gas port 130. The window 150 partitions the second section 140 into a first portion 141 that is located between the window 150 and the port 130 and a second portion 143 that is located between the window 150 and the second end 114.

In the illustrated embodiment, there are two windows 150, 151 with the two windows 150, 151 being separated by a pair of vertical posts 155 that are spaced opposite (180 degrees) one another.

The first portion 141 includes a structure 160 that holds the port 130 in place. For example, the structure 160 can be in the form of a spoked rib construction 165 that extends between the port 130 and an inner surface of the annular shaped first portion 141. Between the spokes 165, open spaces are formed and thus, the first portion 141 is at least substantially hollow and open to permit air flow into the bottom of the housing 110.

Figure 3:
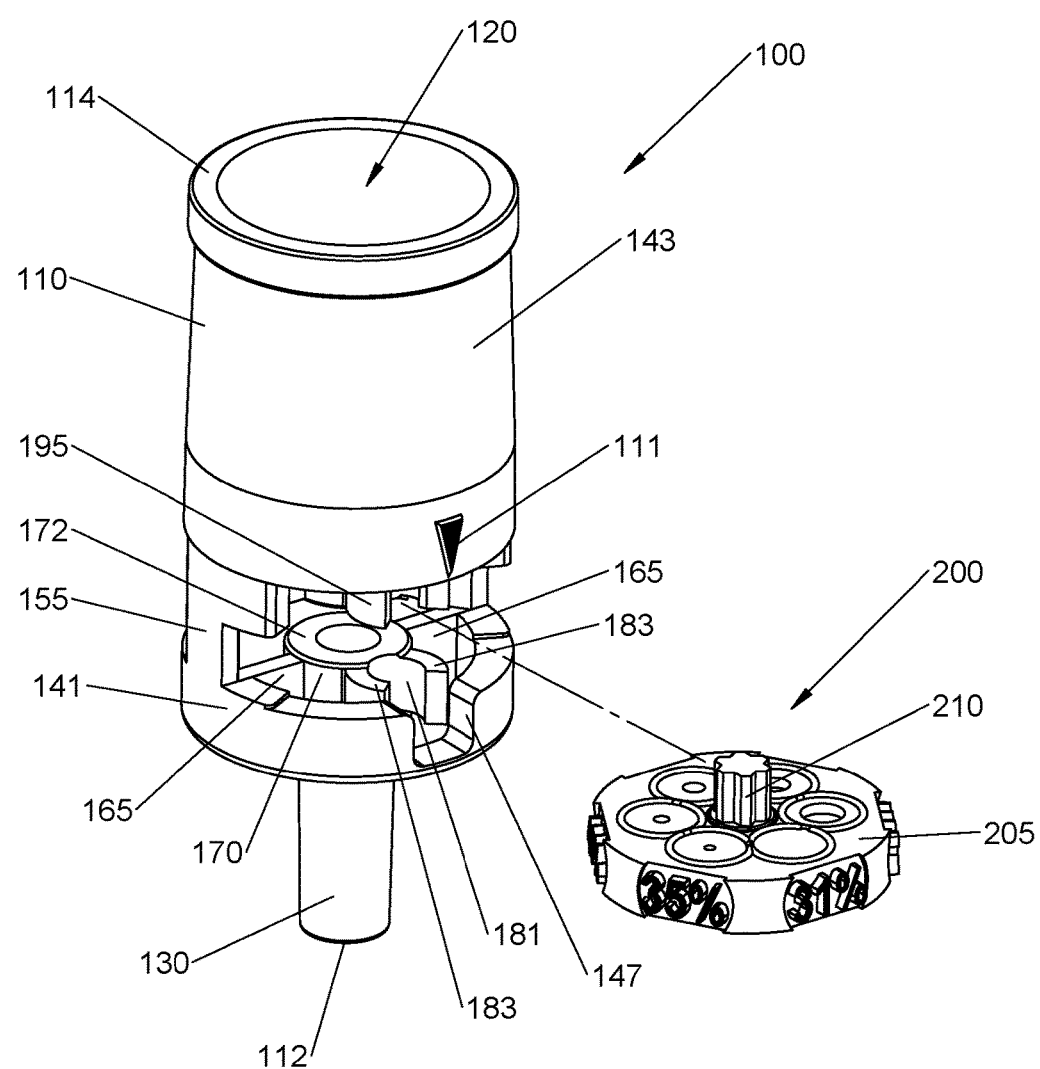
FIG. 3 is an exploded perspective view of the venturi connector with an actuator (selector member) being exploded from a connector body.
Figure 4A:
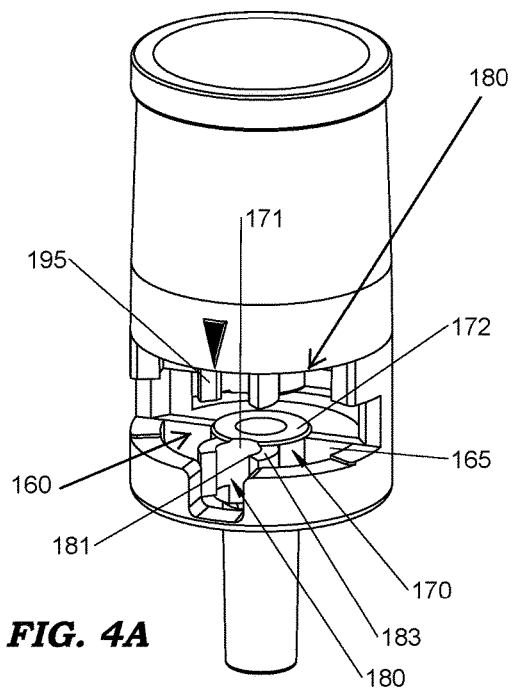
FIG. 4A is side perspective view of the gas delivery venturi connector body of FIG. 1.
Figure 4D:
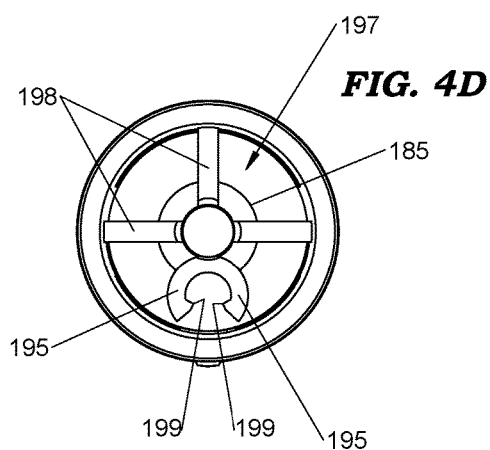
FIG. 4D is a top plan view of the gas delivery venturi connector body of FIG. 1.
Figure 4B:
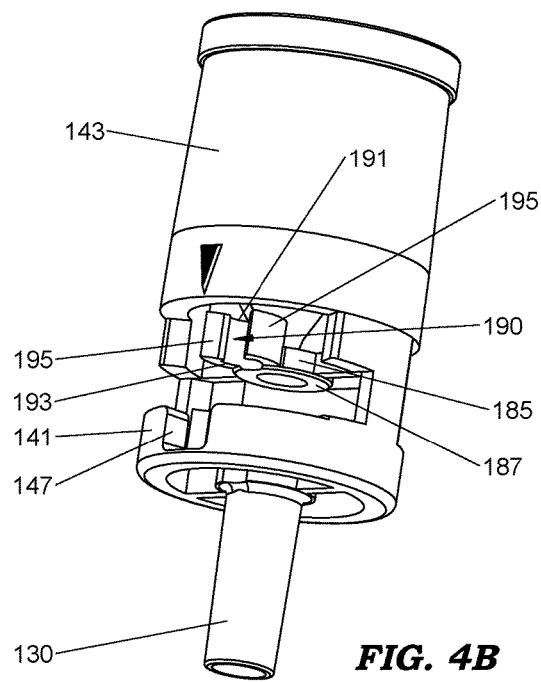
FIG. 4B is side perspective view of the gas delivery venturi connector body of FIG. 1.
Figure 4C:
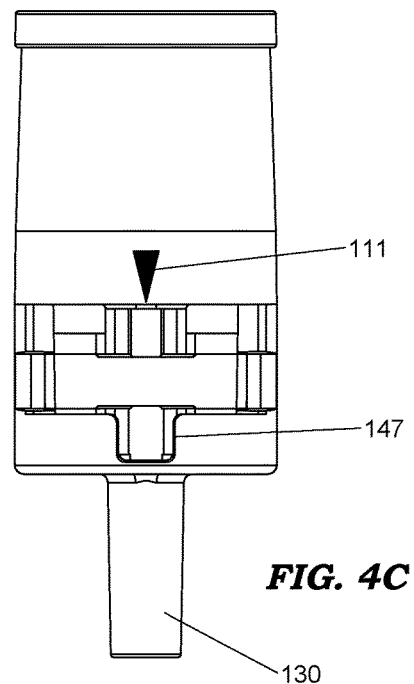
FIG. 4C is side elevation view of the gas delivery venturi connector body of FIG. 1.

As best shown in FIGS. 3-4, a top end of the port 130 defines a lower hub 170 that has an exposed lower sealing surface 172. As shown, the lower hub 170 can be in the form of a top end section of the port 130. As shown, the lower sealing surface 172 can be in the form of an annular shaped exposed surface. The spokes 165 can be seen integrally connected to the lower hub 170 (e.g., can be integrally formed during a common molding process). The lower sealing surface 172 is a flat surface.

The first portion 141 includes additional features as described below. First, the first portion 141 includes a first retention means (member) 180 for securely coupling the adjustable actuator member 200 to the housing 110. The first retention member 180 is in the form of an open collar or open clamp member. The first retention member 180 has an opening or slot 181 formed therein to permit access of a portion of the adjustable actuator member 200. The first retention member 180 is generally C-shaped with the opening 181 defining the break in the first retention member 180. The first retention member 180 is integrally formed with the lower hub 170 (e.g., as by a common molding process). The first retention member 180 generally has a circular shape with the opening 181 being defined as a break within the circular shaped structure. The opening 181 faces outward toward the peripheral edges of the first portion 141 but the first retention member 180 is not in physical contact with the housing 110. The closed rear wall (surface) of the first retention member 180 can be defined by an arcuate shaped cut-out 171 formed in the lower hub 170. In this embodiment, the first retention member 180 is defined by a pair of fingers 183 that are spaced from one another and extend outwardly from the lower hub 170. The fingers 183 and the cut-out in the lower hub form a smooth arcuate shaped surface. The fingers 183 also provide some flexing action since that are only connected at one end to the lower hub 170.

The first portion 141 also includes a cut-out or notch 147 formed therein and open along the outer surface of the housing 110. In particular, the notch 147 can be a U-shaped opening that is formed in the peripheral wall of the housing 110 in the first portion 141 thereof. The notch 147 is thus open along the top thereof due to the presence of window 150 thereabove. The notch 147 is axially aligned with the first retention member 180. The height of the notch 147 and the height of the first retention member 180 are about equal since the notch 147 defines an entrance into the first retention member 180, thereby allowing reception of a portion of the adjustable actuator member 200. More specifically and as described further below, the adjustable actuator member 200 is inserted laterally into the housing 110 through window 150 and by means of the notch 147. The width of the notch 147 is thus greater than or equal to the width of the portion of the adjustable actuator member 200 to allow the portion of the adjustable actuator member 200 to be received within the first retention member 180.

The lower sealing surface 172 is preferably located above the top of the first retention member 180 and the open top of the notch 147.

As shown in FIG. 3, the second portion 143 of the second portion 140 has some internal structures similar to the first portion 141 but represents the entrance into the interior cavity 120 which is in the form of a gas mixing chamber in which the gas flowing through the port 130 mixes with air that flows through the windows 150, 151.

The second portion 143 is a substantially hollow structure since it represents a gas mixing chamber. Similar to the first portion 141, the second portion 143 includes a reinforcement structure 197 that holds an upper hub 185 in place. For example, the structure 197 can be in the form of a spoked rib construction or stiffening gusset structure 198 that extends between the upper hub 185 and an inner surface of the annular shaped second portion 143. Between the spokes 198, open spaces are formed and thus, the second portion 143 is at least substantially hollow and open to permit air flow into the mixing chamber 120 which lies directly above the upper hub 185.

Similar to the lower hub 170, the upper hub 185 has an annular shape with a center bore (flow hole) formed therein. The lower hub 170 and upper hub 185 lie in parallel planes with respect to one another with a space (D1) formed therebetween. The space D1 is selected to receive a main body portion 205 of the adjustable actuator member 200 and securely position the actuator member 200 therebetween, while allowing the actuator member 200 to move (rotate) within the housing 110.

The upper hub 185 is axially aligned with the lower hub 170 to allow the gas from the gas source to flow through the gas port 130, through the actuator member 200 (as described below) and through the upper hub 185 and into the gas mixing chamber 120. The reinforcement structures 165 and 197 thus centrally locate the two hubs 170, 185 within the housing 110.

As best shown in FIGS. 4A-D, the upper hub 185 has an exposed upper sealing surface 187. As shown, the upper sealing surface 187 can be in the form of an annular shaped exposed surface. The spokes (gussets) 197 can be seen integrally connected to the upper hub 185 (e.g., can be integrally formed during a common molding process). The upper sealing surface 187 is a flat surface.

Similar to the lower hub 170, the upper hub 185 includes a second retention means (member) 190 for securely coupling the adjustable actuator member 200 to the housing 110. The second retention member 190 is in the form of an open collar or open clamp member. The second retention member 190 has an opening or slot 191 formed therein to permit access of a portion of the adjustable actuator member 200. The second retention member 190 is generally C-shaped with the opening 191 defining the break in the second retention member 190. The second retention member 190 is integrally formed with the upper hub 185 (e.g., as by a common molding process). The second retention member 190 generally has a circular shape with the opening 191 being defined as a break within the circular shaped structure. The opening 191 faces outward toward the peripheral edges of the second portion 143 but the second retention member 190 is not in physical contact with the housing 110. The opening 191 overlies the opening 181 of the first retention member 180.

The closed rear wall (surface) of the second retention member 190 can be defined by an arcuate shaped cut-out 193 formed in the upper hub 185. In this embodiment, the second retention member 190 is defined by a pair of fingers 195 that are spaced from one another and extend outwardly from the upper hub 185. The fingers 195 and the cut-out in the upper hub form a smooth arcuate shaped surface. The fingers 195 also provide some flexing action since they are only connected at one end to the upper hub 185.

As described below, the first and second retention members 180, 190 can be constructed such that they function as snap-fit coupling members in that portions of the actuator member 200 are snap-fittingly received and mated thereto. Preferably, the coupling between the actuator member 200 and the housing 110 is of a type that prevents the subsequent removal of the actuator member 200 from the housing 110 after insertion therein. In other words, the actuator member 200 is intended to be inserted and locked in place with respect to the housing 110 to form a disposal product that is discarded after use.

The inner cavity (mixing chamber) 120 is located above both the upper hub 185 and second retention member 190, as well as above the reinforcement structure 197. As mentioned, there are open spaces formed around the reinforcement structure 197 to allow air to flow therethrough into the mixing chamber 120. More specifically, air that flows through the air entrainment windows 150, 151 flows into the mixing chamber 120.

In accordance with the present invention, the second retention member 190 includes detents 199 located at but not limited to the free ends of the fingers 195. As described below, these detents 199 not only provide a locking means but they also provide tactile feedback to the user as the actuator member 200 is moved within the housing 110. While the fingers 183 are shown to not include detents, detents can be provided thereon similar to the detents 199.

The housing 110 also includes indicia 111 formed thereon for indicating the setting (rotational location) of the actuator member 200 within the housing 110. In the illustrated embodiment, the indicia 111 is in the form of a downward pointing arrow. In particular, the arrow 111 points down toward to the notch 147 and thus also points to and is axially aligned with the upper hub 185 and lower hub 170.

As discussed herein, the port 130, lower hub 170 and upper hub 185 define a flow path for the supplemental gas (e.g., oxygen) that is being delivered from the gas source to the mixing chamber 120 for mixing with air that is entrained and flows through the windows 150, 151 (and through other openings formed in the housing 110) to the mixing chamber 120.

Figure 6A:
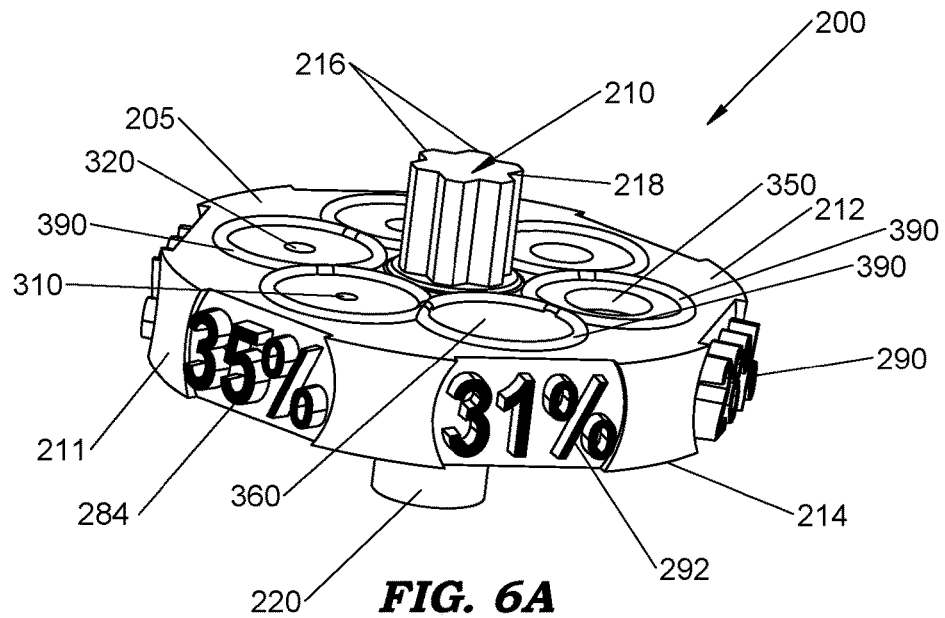
FIG. 6A is a side perspective view of the actuator (selector member)
Figure 6B:
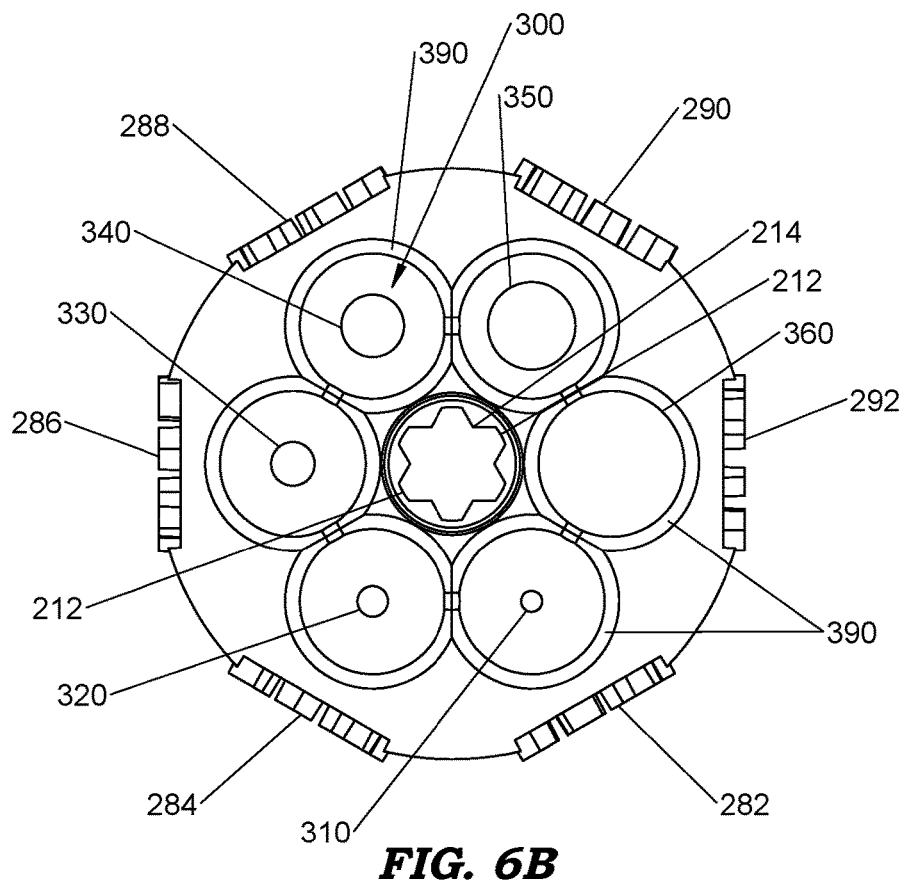
FIG. 6B is a top plan view of the actuator (selector member)
Figure 7A:
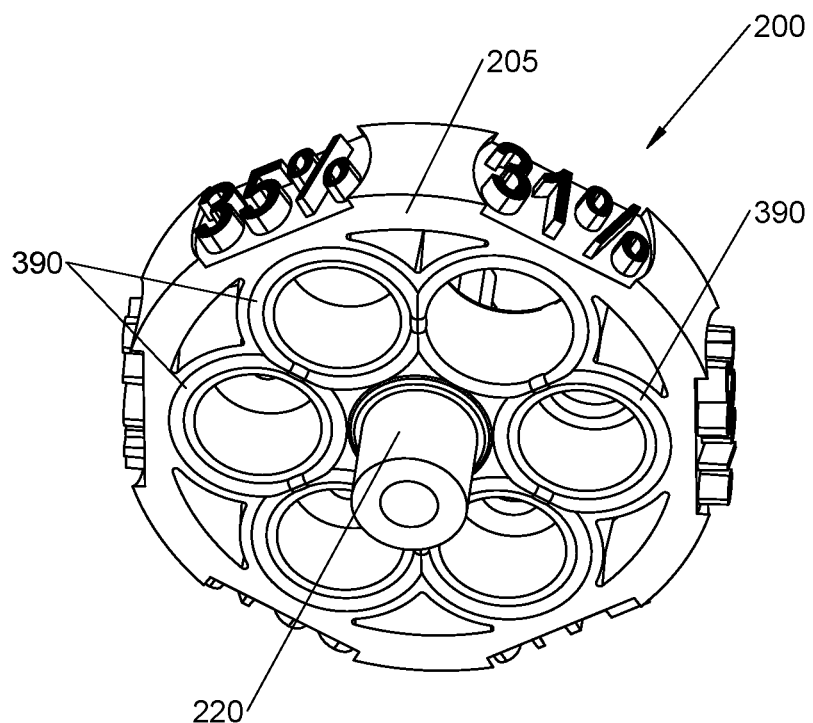
FIG. 7A is a bottom perspective view of the actuator (selector member)
Figure 7B:
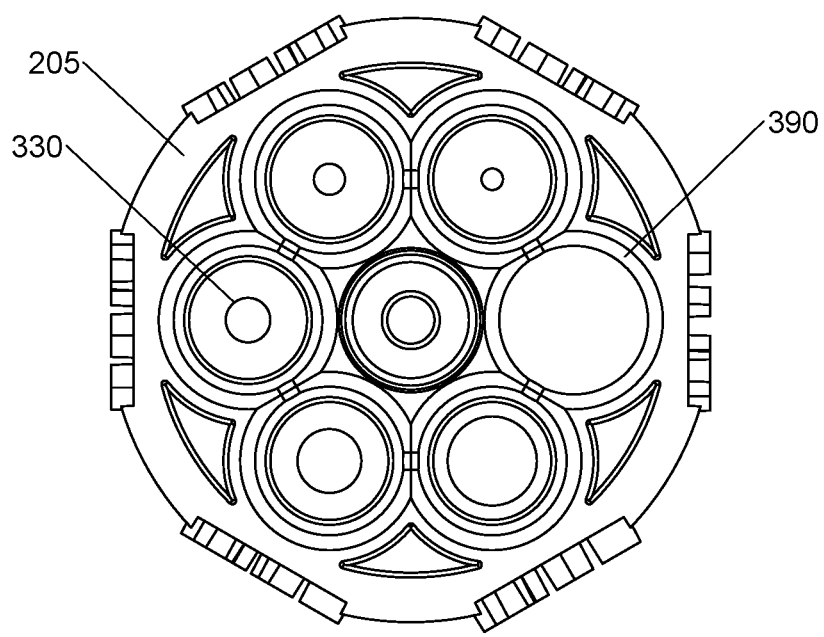
FIG. 7B is a bottom plan view of the actuator (selector member)

As best shown in FIGS. 6-7, the adjustable actuator member 200 includes a body 205 that has a top surface 212 and an opposing bottom surface 214. When the actuator member 200 is inserted into the housing 110, the top surface 212 faces upward toward the upper hub 185 and the bottom surface 214 faces toward the lower hub 170. The body 205 has a peripheral edge 211. In the illustrated embodiment, the body 210 has a generally circular shape. The actuator member 200 includes a central shaft about which it moves when coupled to the housing 110. As shown, the central shaft can be formed of a first shaft section (upper shaft section) 210 that extends outwardly from the top surface 212 and a second shaft section (bottom shaft section) 220 that extends downwardly from the bottom surface 214. The first and second shaft sections 210, 220 are axially aligned and centrally located with respect to the body 205.

The second shaft section 220 can thus be in the form of a cylindrically shaped post. As illustrated, the outer surface of the second shaft section 220 can be a smooth surface. In contrast, the first shaft section 210 has a contoured outer surface that is complementary to the shape of the detents 199. More specifically and as shown, the first shaft section 210 can be a ribbed structure and be formed of a plurality of axially extending ridges (detents) 216 formed along the length of the first shaft section 210. As shown in FIGS. 6A-B, between adjacent ridges (detents) 216, valleys or pockets 218 are formed. The ridges 216 are formed in view of the detents 199 such that the detent 199 engages the ridges 216 in a locking manner yet the first shaft section 210 can be advanced (rotated) in a ratchet like manner. The ridges 216 and detent 199 thus are similar to a pawl/teeth arrangement in a ratchet environment. However, the first shaft section 210 can be rotated in both a clockwise direction and a counter clockwise direction.

One of the primary features of the ridges 216 is to provide tactile feedback to the user in that as the second shaft section 220 is advanced (rotated), the user feels the engagement between the ridges 216 and the detents 199. This provides tactile confirmation to the user that the actuator member 200 has been advanced. The momentary locking between the ridges 216 and detents 199 also provides a locating and retention means for holding the actuator member 200 in one discrete position within the housing 110.

Though the detent 199 and the ridge (detents) 216 are shown integral to second retention member 190 and shaft section 210, they could be added to first retention member 180 and second shaft section 220 to provide a more robust ratcheting and tactile feedback mechanism.

A plurality of jets or nozzles 300 are formed within the body 210 at select locations about the first and second shaft sections 210, 220. For example and as shown, the jets or nozzles 300 can be formed circumferentially about the first and second shaft sections 210, 220. Each of the jets/nozzles 300 has its own flow construction so as to produce a desired flow rate therethrough. The jets/nozzles 300 can be thought of as being venturi orifices.

In the illustrated embodiment, the body 210 has six (6) jets/nozzles 300 formed therein, with each jet/nozzle 300 having an associated flow rate. More specifically, the body 205 has formed therein a first nozzle (venturi orifice) 310; a second nozzle (venturi orifice) 320; a third nozzle (venturi orifice) 330; a fourth nozzle (venturi orifice) 340; a fifth nozzle (venturi orifice) 350; and a sixth nozzle (venturi orifice) 360. As will be appreciated, the sizes of the orifices of the respective nozzles vary to produce different gas flow rates. As the size (diameter) of the orifice increases, the flow rate likewise increases. The size of the orifice progressively increases from the first nozzle 310 to the sixth nozzle 360. In other words, the first nozzle 310 has the smallest sized orifice, while the sixth nozzle 360 has the largest sized nozzle. The orifices are centrally located within the individual nozzles 300. Each of the jets/nozzles 300 includes a seal member 390 formed therearound both along the top surface 312 and the bottom surface 314. The seal member 390 can be formed of the same material that forms the body of the actuator member or it can be formed of a different material. For example, the seal member 390 can be formed of a conventional sealing material, such as rubber or a polymeric material. The seal member 390 functions as an O-ring or the like and provides a seal.

The actuator member 200 is disposed within the housing 110 by being inserted into the window 150. In particular, the actuator member 200 is held upright and the second shaft section 220 is passed through the notch 147. The second shaft section 220 is introduced through the opening 181 of the first retention member 180. The fingers 183 have a degree of flexibility and flex outwardly to allow the second shaft section 220 to pass into the first retention member 180 (between the fingers 183) and once the shaft clears, the fingers 183 flex back to capture the second shaft section 220. Similarly, the first shaft section 210 is received into the second retention member 190 by passing through the opening 191 between the fingers 195. The fingers 195 flex outwardly to allow reception of the first shaft section 210 and once the shaft clears, the fingers 195 flex back to capture the first shaft section 210.

The detents 199 of the second retention member 190 engage the ridges 216 of the first shaft section 210 for securely locking the actuator member 200 in place.

The actuator member 200 is eccentrically mounted within the housing 110 and in particular, the actuator member 200 is constructed and is mounted in the housing 110 in such a way that one of the nozzles 310, 320, 330, 340, 350, 360 is axially and fluidly aligned with the lower hub 170 and the upper hub 185. The nozzle that is in fluid registration with the lower hub 170 and the upper hub 185 is the nozzle that is currently selected and active in that it is located within the flow path of the gas from the gas source to the mixing chamber 120 and thus, serves to restrict the flow of the gas according to the characteristics (e.g., size) of the orifice.

As a result of this eccentric orientation, a portion of the body 205 of the actuator member 200 extends beyond the peripheral side of the housing 110 as shown. The actuator member 200 is thus coupled to the housing 110 in such a manner that as the body 205 is rotated within the retention members 180, 190, the individual nozzles 300 are brought into fluid communication with the bores formed within hubs 170, 185. However, at any one time, only a single nozzle is in fluid registration with the hubs 170, 185. This single nozzle can be referred to as the selected nozzle since it is the only nozzle amongst the group that is actively metering and controlling the flow rate of the supplemental gas as it is delivered to the mixing chamber 120. As the actuator member 200 is rotated, clicks are felt by the user as a result of the detents 199 engaging the ridges 216.

A sealing action is provided between the upper sealing surface 187 and one seal member 390 and similarly between the lower sealing surface 172 and one seal member 390. This sealing action prevents any gas from escaping between the interfaces between the body 205 of the actuator member 200 and the lower hub 170 and upper hub 185 as the gas flows from the port 130 through the selected nozzle and into the mixing chamber 120.

The venturi connector 100 of the present invention thus permits the user to select the supplemental gas (oxygen) concentration that is delivered to the patient. The nozzles 300 can be constructed such that the sizes of the orifices results in the first nozzle 310 delivering 24% oxygen; the second nozzle 320 delivering 28%; the third nozzle 330 delivering 31%; the fourth nozzle 340 delivering 35%; the fifth nozzle 350 delivering 40% and the sixth nozzle 360 delivering 50%. It will be appreciated that the following is merely an exemplary construction and not limiting since the nozzles 300 can be constructed to produce any number of flow rates and oxygen delivery concentrations.

To change the flow rate of the gas (oxygen) being injected into the mixing chamber 120, the user simply adjusts the flow rate to port 130 and rotates the actuator member 200 until the appropriate nozzle is in fluid registration with the hubs 170, 185.

The figures show the difference between the two windows 150, 151. In particular, the window 150 is obstructed at least partially by the actuator member 200 since the actuator member 200 is received within the window 150. In contrast, the actuator member 200 does not extend into the window 151 and therefore, the window 151 is more open and serves more as an air entrainment window to allow air to flow into the mixing chamber 120. Air thus is drawn into the window 151 and flows through the open spaces between the spokes 198 and directly into the mixing chamber 120 which is located above the upper hub 185. The bore formed in the upper hub 185 is open at the top of the upper hub 185 and therefore, this defines the exit port of the gas (oxygen) flowing through the port 130 and through the nozzle 300 of the actuator member 200 and allows the gas to flow into the mixing chamber 120 where it mixes with the air being entrained through the windows 150, 151.

The peripheral edge 211 of the body 210 includes indicator indicia 280 that relates to the characteristics of the individual nozzles 300. For example, as illustrated, the nozzle 310 includes first indicia 282 disposed proximate thereto (adjacent thereto); the nozzle 320 includes second indicia 284; the nozzle 330 includes third indicia 286; the nozzle 340 includes fourth indicia 288; the nozzle 350 includes fifth indicia 290; and the nozzle 360 includes sixth indicia 292. The indicia indicates a flow rate of one corresponding orifice.

In accordance with the present invention and as discussed below, the indicia is offset relative to the nozzle to which it relates and to which is designates the oxygen concentration. In other words, the first indicia 282 that is physically next to the first nozzle 310 in fact indicates the flow rate of the nozzle 340 which is 180 degrees away from the first indicia 282; the second indicia 284 that is physically next to the second nozzle 320 in fact indicates the flow rate of the nozzle 350; the third indicia 286 that is physically next to the third nozzle 330 in fact indicates the flow rate of the nozzle 360; the fourth indicia 288 that is physically next to the fourth nozzle 340 in fact indicates the flow rate of the nozzle 310; the fifth indicia 290 that is physically next to the fifth nozzle 350 in fact indicates the flow rate of the nozzle 320; and the sixth indicia 292 that is physically next to the sixth nozzle 360 in fact indicates the flow rate of the nozzle 330. In other words, the indicia is located 180 degrees from the nozzle to which it relates and as a result of the active nozzle being located centrally within the housing 110 in registration with the hubs 170, 185, its correlating indicia is located on the periphery of the body 205 180 degrees from the active nozzle (i.e., the indicia is located on the portion of the actuator member 200 that overhangs the housing 110).

The present invention thus provides a compact multi-nozzle venturi connector 100 that overcomes the disadvantages associated with the prior art, especially the need for having a kit of multiple connectors when only a single connector may be needed and used. In this present invention, a single device is provided and the user can simply manipulate the actuator member 200 to cause the desired nozzle 300 to be placed in the active position in which the gas flows therethrough and is metered to achieve the desired oxygen concentration/flow rate to the patient.

It will be appreciated and understood that the second end 114 of the housing 110 can be connected either directly or indirectly to the face mask using a tube, such as a corrugated tube, etc., that is connected to an inhalation inlet of the face mask. However, other means for connecting the two can be used.

Figure 8:
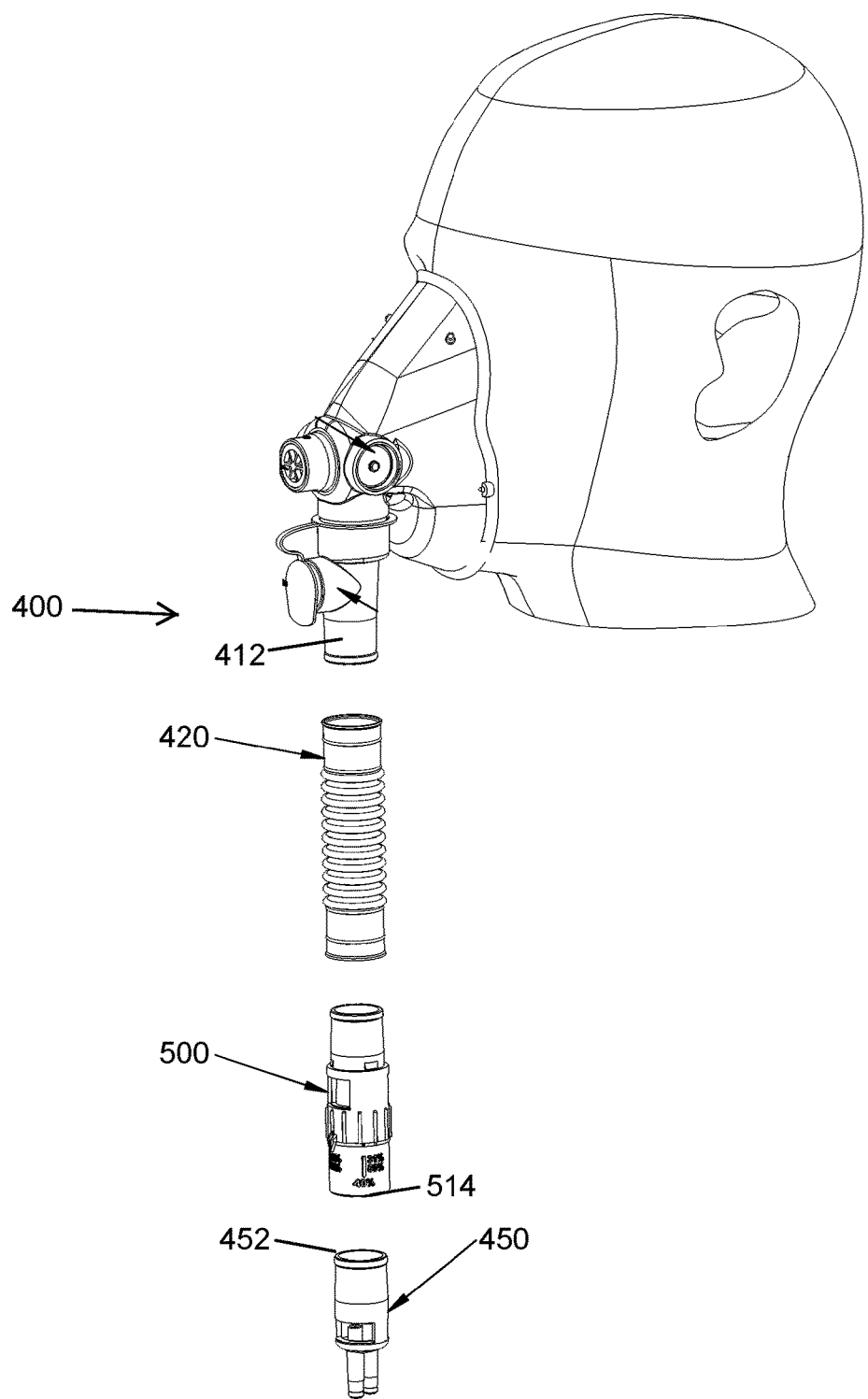
FIG. 8 is an exploded perspective view of a venturi assembly in accordance with another embodiment of the present invention.

FIG. 8 is an exploded perspective view of a venturi assembly 400 in accordance with another embodiment of the present invention. The assembly 400 is formed of a number of parts (components) that interact with one another to provide for controlled gas delivery to a patient. The assembly 400 is meant for use with a patient interface member (assembly) 410 that is designed to interact with the patient and in one exemplary embodiment, the interface member 410 is in the form of a mask assembly. It will be appreciated that the illustrated interface member 410 is merely exemplary in nature and any number of other types of interface members can be used for delivering gas to the patient. The interface member 410 includes a main port 412 for receiving the gas from the venturi assembly 400. An elongated conduit member 420 is connected to the main port 412 and to the venturi assembly 400 for delivering the gas from the venturi assembly 400 to the interface member 410. The elongated conduit member 420 can be in the form of an elongated tube which can be of a type which is expandable/retractable in that a length of the elongated conduit member 420 can be varied. Conventional methods of attachment can be used to attach the elongated conduit member 420 to both the interface member 410 and the venturi assembly 400 (e.g., conical fitting, frictional fit, snap, etc. . . . ).

Figure 9:
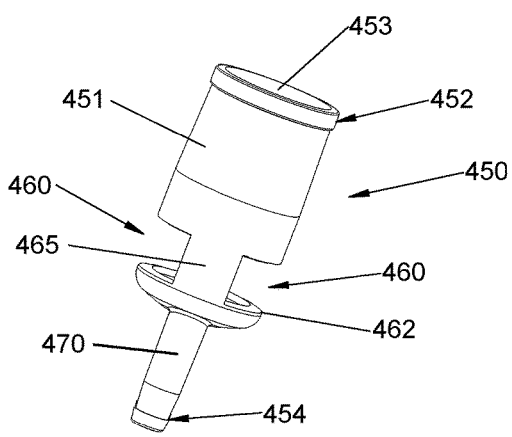
FIG. 9 is a side perspective view of a multi-port venturi member that is part of the venturi assembly of FIG. 8.

FIGS. 8-20 illustrate in more detail the venturi assembly 400 according to one embodiment of the present invention. The venturi assembly 400 is formed of two main components, namely, a multi-port venturi member 450 and a secondary gas entrainment valve member 500. FIG. 9 shows the multi-port venturi member 450 according to one embodiment. The multi-port venturi member 450 has a first end 452 and an opposite second end 454. The multi-port venturi member 450 is a generally hollow body 451 that includes a main hollow space 453 at the first end 452. In the illustrated embodiment, the body 451 has a cylindrical shape; however, it will be appreciated that the body 451 can have any number of other shapes.

The body 451 also has an air entrainment window 460 formed therein below the main hollow space 453. The air entrainment window 460 is thus located intermediate to the ends 452, 454. The member 450 also includes a lower body section 462 that is connected to the hollow body 451 by means of a pair of opposing walls 465 (e.g., a pair of vertical walls located 180 degrees apart). The walls 465 thus partially define the air entrainment window 460. The lower body section 462 is a disk shaped structure that lies below the air entrainment window 460 and serves as a floor of the air entrainment window 460. The air entrainment window 460 is thus open to atmosphere and serves to allow air to flow into the hollow space 453 and then flow ultimately to the patient (by means of the elongated conduit member 420 and the interface member 410).

The member 450 also includes at least one and preferably a plurality of gas port members 470, 480 that extend downwardly from the lower body section 462. The gas port members 470, 480 are configured to be individually connected to a gas source (such as an oxygen gas source). As shown in the cross-sectional view of FIG. 12, the gas port members 470, 480 are elongated hollow conduits that each allows a fluid, such as gas (oxygen), to enter at an exposed, free distal end 472, 482 and flow therethrough into the hollow space 451 while flowing by the air entrainment window (which is designed to allow atmospheric gas (air) to be entrained by the gas flow through the gas port members 470, 480). Entrainment of air through the window 460 results due to the pressure drop created by the gas that flows through either of the gas port members 470, 480. The distal ends 472, 482 can be barbed ends to facilitate mating of the gas port members 470, 480 to conduits (tubing) that is connected to the same, single gas source or to multiple gas sources.

In another embodiment, the member 450 includes only a single gas port member.

It will be understood that at any one operating time, gas is flowing through only one of the gas port members 470, 480. As described below, the gas port members 470, 480 have different gas flow characteristics and therefore, depending upon the desired gas concentration that is chosen to be delivered to the patent, the user selects one of the gas port members 470, 480 to use. Once again, at any one point in time, only one of the gas port members 470, 480 is active in that gas is flowing therethrough.

Figure 11:
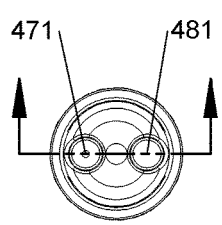
FIG. 11 is a top plan view of the multi-port venturi member of FIG. 10.
Figure 10:
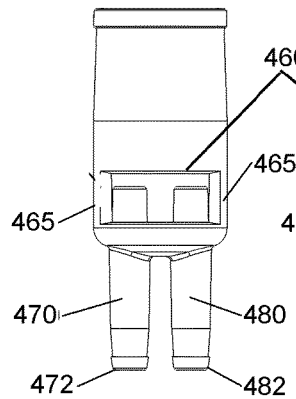
FIG. 10 is a side elevation view of the multi-port venturi member of FIG. 9 and according to a first embodiment.
Figure 12:
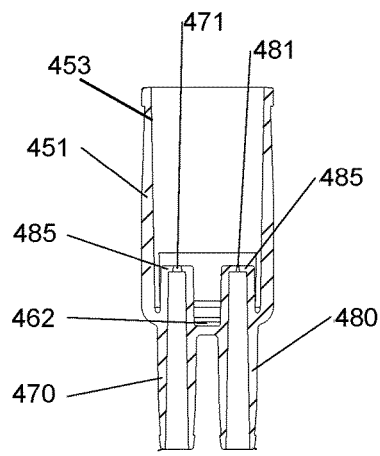
FIG. 12 is a cross-sectional view of the multi-port venturi member taken along the lines 12-12 of FIG. 11.

As best shown in FIGS. 10-12, the gas port members 470, 480 are constructed so as to provide a known gas flow rate. In particular, a top wall 485 is formed across the tops of the gas port members 470, 480 and defines the ceiling of the gas port members 470, 480. An orifice (through hole) 471, 481 is formed in the top walls 485 of the gas port members 470, 480, respectively. The shape and dimensions of the orifices 471, 481 define the gas flow rates of the gas port members 470, 480 and more particularly, by varying the shape and size of the orifices, the gas flow rate associated with the gas port member is likewise changed.

As a result, the gas port member 470 has one associated gas flow rate, while the gas port member 480 has a different gas flow rate associated therewith. It will be appreciated that the system 400 can include a plurality of single or multi-port venturi members 450 that can be grouped as a kit. This allows the user to select the venturi member 450 that has the desired, chosen gas flow rate. The venturi members 450 can be interchanged as part of the overall system 400 depending upon the precise application and desired gas concentration to be delivered to the patient.

As best shown in the cross-sectional view of FIG. 12, first lengths of the elongated gas port members 470, 480 are located above the lower body section 462 and second lengths of the elongated gas port members 470, 480 are located below the lower body section 462 (which is generally in the form of a disk that defines a floor of the member). The second lengths are greater than the first lengths and therefore, more of the gas port members 470, 480 are located below the lower body section 462. The lower body section 462 defines a solid wall structure between the gas port members 470, 480. The tops of the gas port members 470, 480 are disposed within the air entrainment window. In other words, the height of the gas port members 470, 480 is such that the tops are disposed within the air entrainment window and therefore, gas exiting the top of one of the gas port members 470, 480 is mixed with entrained air flowing into the air entrainment window 460.

The gas flow rates associated with the gas port members 470, 480 can be the same or as shown in FIGS. 10-12, the flow rates can be different. FIGS. 10-12 illustrate a laterally disposed gas injection arrangement in which the gas port members 470, 480 are located adjacent the vertical walls 465 as best shown in FIG. 10 and the orifices 471, 481 are centrally located with respect to gas port members 470, 480. The orifice 471 has a greater size than the orifice 481 and therefore, has a greater associate gas flow rate. It will be appreciated that the orifices 471, 481 thus serve to meter the gas from the gas source as it flows through the gas port members 470, 480 into the hollow space 451.

In the embodiment of FIGS. 10-12, the gas port members 470, 480 are thus not located directly within the air entrainment window due to the members 470, 480 being disposed adjacent the vertical walls 465.

Figure 14:
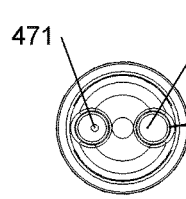
FIG. 14 is a top plan view of the multi-port venturi member of FIG. 13.
Figure 13:
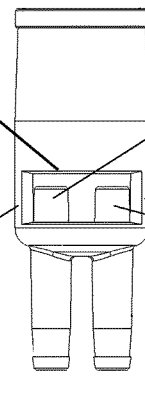
FIG. 13 is a side elevation view of the multi-port venturi member according to a second embodiment.

FIGS. 13-14 show a different embodiment and in particular, show laterally disposed eccentric gas injection. As with FIGS. 10-12, the gas port members 470, 480 are disposed laterally in that these members are formed adjacent the vertical walls 465; however, in this embodiment, the orifices 471, 481 are not located centrally within the gas port members 470, 480, respectively. Instead, the orifices 471, 481 are eccentrically formed within the gas port members 470, 480.

Figure 16:
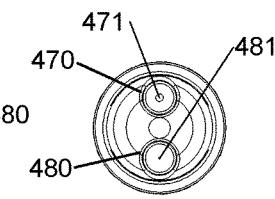
FIG. 16 is a top plan view of a multi-port venturi member of FIG. 15.
Figure 15:
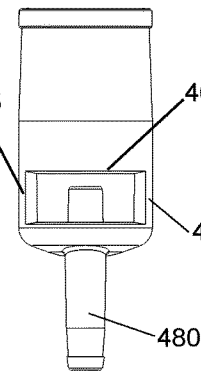
FIG. 15 is a side elevation view of the multi-port venturi member according to a third embodiment.

FIGS. 15-16 show a different embodiment and in particular, show centrally disposed gas injection. Opposite to the arrangement shown in FIGS. 10-12, the gas port members 470, 480 in FIGS. 15-16 are disposed centrally in that the gas port members 470, 480 are not located adjacent the pair of vertical walls 465 as best shown in FIG. 15. Instead, the gas port members 470, 480 are located offset from the vertical walls 485 and are disposed directly within the air entrainment window 460. The orifices 471, 481 are located centrally within the gas port members 470, 480, respectively.

Figure 18:
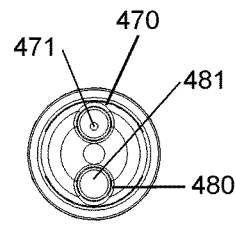
FIG. 18 is a top plan view of the multi-port venturi member of FIG. 17.
Figure 17:
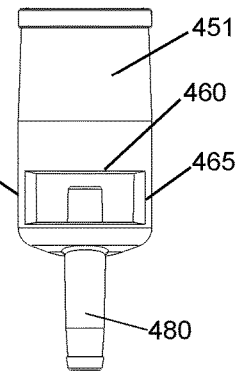
FIG. 17 is a side elevation view of the multi-port venturi member according to a fourth embodiment.

FIGS. 17-18 show a different embodiment and in particular, show centrally disposed eccentric gas injection. Opposite to the arrangement shown in FIGS. 10-12, the gas port members 470, 480 in FIGS. 17-18 are disposed centrally in that the gas port members 470, 480 are not located adjacent the pair of vertical walls 465 as best shown in FIG. 17. Instead, the gas port members 470, 480 are located offset from the vertical walls 465 and are disposed directly within the air entrainment window 460. Unlike the centrally disposed gas injection of FIGS. 15 and 16, the orifices 471, 481 in FIGS. 17 and 18 are eccentrically formed within the gas port members 470, 480.

It will be appreciated that the relative sizes of the orifices 471, 481 are merely exemplary in nature and the sizes of orifices 471, 481 can be readily changed. For instance, the orifice 481 can be larger in size than orifice 471.

In one exemplary embodiment, the outside periphery of end 452 has a diameter of about 22 mm.

Figure 19:
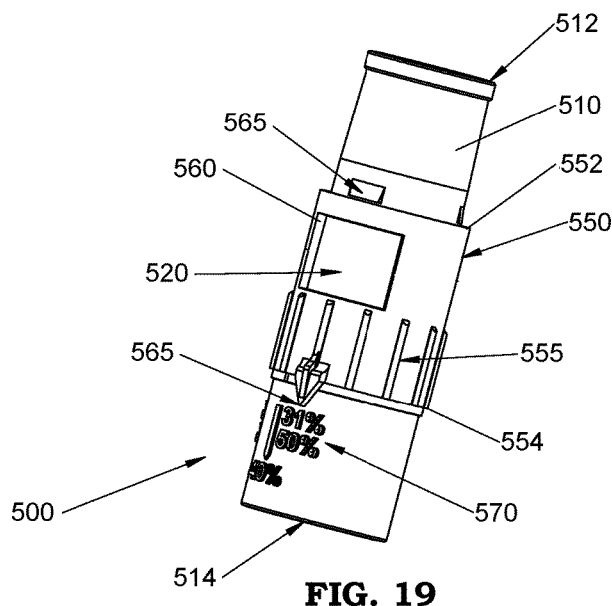
FIG. 19 is a side perspective view of a secondary gas entrainment valve member that is part of the assembly of FIG. 8.

FIG. 19 shows the secondary gas entrainment valve member 500 which is formed of a generally hollow body 510 that has a first end 512 and an opposing second end 514. As shown in FIG. 8, the second end 514 is configured to mate with the first end 452 of the multi-port venturi member 450. The second end 514 can be a female connector type, while the first end 452 of the multi-port venturi member 450 is of a male connector type. Similarly, the first end 512 can be a male connector type that is designed to mate with the elongated conduit member 420. The first end 512 can thus have smaller dimensions compared to the second end 514.

The generally hollow body 510 has a secondary air entrainment window 520 formed integrally therein. The air entrainment window 520 extends circumferentially about the body 510 and thus is defined by a first end (in the form of a vertical edge) and a second end (in the form of a vertical edge). The air entrainment window 520 is intended to allow atmospheric gas (air) to flow into the hollow interior of the body 510 where in mixes with the gas that flows out of the multi-port venturi member 450 (which one will appreciate is already mixed gas due to air being entrained through the air entrainment window 460 (which can be thought of as being a main or primary air entrainment window). The air entrainment window 520 is a secondary entrainment window since it serves as a second window between the gas source and the patient interface 410 in which air can be entrained through to mix with the gas for purposes of altering the characteristics, and in particular, the gas concentration, of the gas that is delivered to the patient.

In accordance with the present invention, the secondary gas entrainment valve member 500 includes a rotatable shutter 550 that is rotatably and cylindrically coupled to the body 510 and more specifically, the shutter 550 is disposed about the body 510 in the location of the air entrainment window 520 to allow the shutter 550 to either open or close the secondary gas entrainment window 520 depending upon the desired setting as described below. The shutter 550 has a first (top) end 552 and an opposite second (bottom) end 554.

Any number of different techniques for coupling the shutter 550 to the body 510 can be used. For example, different types of mechanical attachment techniques can be used including a friction fit, a snap fit, etc. In FIG. 19, the body 510 includes a shutter retaining mechanism in the form of tabs 565 spaced apart from one another and located circumferentially about the body 510. The top end 552 of the shutter 550 is located below the tabs 565.

The shutter 550 itself has an air entrainment window 560 formed therein. The air entrainment window 560 is defined by a first end 562 (vertical wall) and a second end 564 (vertical wall).

There is a correlation between the degree of registration between the air entrainments windows 520, 560 and more particularly, the degree of overlap and the openness of the two windows 520, 560, which factors into the amount of air being entrained through the secondary gas entrainment valve member 500 and thus, the concentration of the gas delivered to the patient. The height of the window 560 is preferably equal to or greater than the height of the window 520 and preferably, the length of the window 560 is preferably equal to or greater than the length of the window 520.

The shutter 550 rotates about the body 510 as mentioned above and therefore, the shutter 550 can include features 555 (means) to assist the user in rotating the shutter 550. In particular, the features 555 can be in the form of ribs that are spaced apart and extend circumferentially about the shutter 550. The ribs 555 are raised structures that permit the user to more easily grip and rotate the shutter 550 relative to the body 510.

The secondary gas entrainment valve member 500 also preferably includes indicia 570 to allow the user to set the degree of air entrainment and thus, to position the secondary gas entrainment valve member 500 at a setting that achieves the desired gas concentration being delivered to the patient. The indicia 570 are also raised structures that permit the user to more easily grip the body 510 while rotating the shutter 550 to achieve the desired gas concentration.

For example, the shutter 550 can include a gas concentration pointer 565 that is formed along the bottom edge 554 of the shutter 550 and the lower region of the body 510 includes gas concentration indicator markings 570. For example, the markings 570 include a plurality of gas concentrations (in percentages) that correspond to the concentration of the gas that is delivered to the patient. The markings 570 directly correspond to the degree of overlap between the windows 520, 560 in that the greater the overlap (registration) between the windows 520, 560, the greater the openness of the secondary air entrainment window resulting in a greater flow of atmospheric air into the member 500 (thereby resulting in a reduced gas concentration being delivered to the patient as a result of more mixing between atmospheric gas and the mixed gas from the multi-port venturi member 450).

The rotatability of the shutter 550 allows the user to effectively and easily "dial in" the desired gas concentration for delivery to the patient by simply rotating the shutter 550 to cause the pointer 565 to point to the desired, selected gas concentration indicator marking 570 (which has the desired gas concentration indicia listed). This results in the window being open the proper desired amount to achieve the target mixing, etc.

FIGS. 20A-20D shows the various operating states of the secondary gas entrainment valve member 500.

Figures 20A, 20B, 20C, 20D:
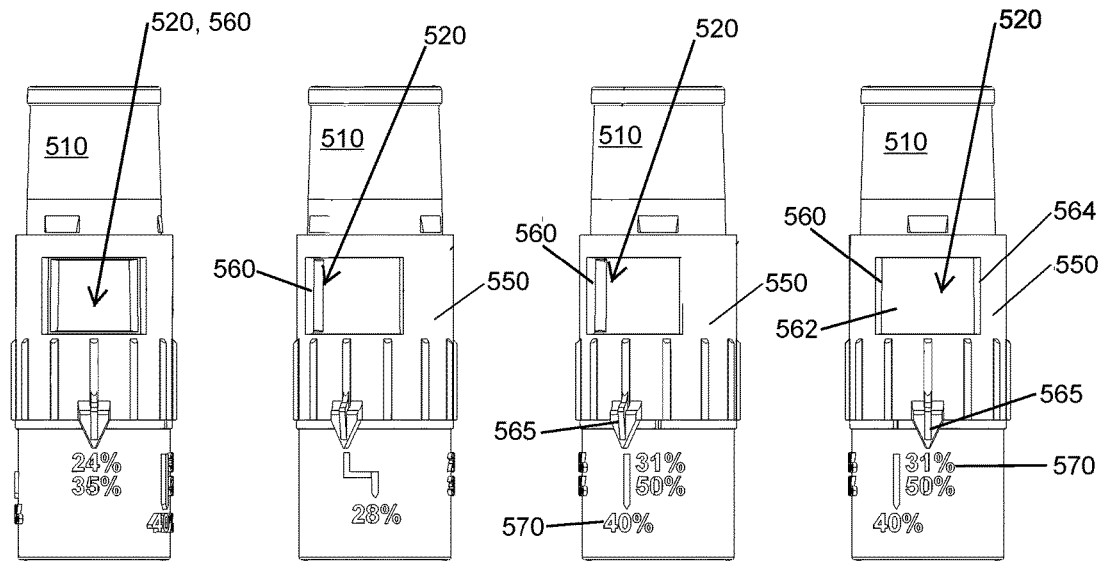
FIG. 20A is a side elevation view showing the secondary gas entrainment valve member in a fully open position.
FIG. 20B is a side elevation view showing the secondary gas entrainment valve member in a partially open position.
FIG. 20C is a side elevation view showing the secondary gas entrainment valve member in a partially open position.
FIG. 20D is a side elevation view showing the secondary gas entrainment valve member in a fully closed position.

FIG. 20A shows the air entrainment port in a fully opened position (i.e., complete registration between the windows 520, 560). As will be seen in FIG. 20A, the markings 570 include two numbers, namely, a first number that is disposed on top of a second number. These two numbers correspond to the gas concentrations (%) that are obtained depending upon which of the gas port members 470, 480 of the venturi member 450 is used and the desired gas concentration to be delivered. In the example shown in FIG. 20A, the second number (35%) corresponds to the gas port member 470 (which has a larger orifice 471 compared to the orifice 481 of gas port member 480). The first number (24%) corresponds to the gas concentration obtained with gas port member 480.

FIG. 20D shows the air entrainment port in a fully closed position (i.e., complete registration between the windows 520, 560). As will be seen in FIG. 20D, the markings 570 include two numbers, namely, a first number that is disposed on top of a second number. These two numbers correspond to the gas concentrations (%) that are obtained depending upon which of the gas port members 470, 480 of the venturi member 450 is used and the desired gas concentration to be delivered. In the example shown in FIG. 20D, the second number (50%) corresponds to the gas port member 470 (which has a larger orifice 471 compared to the orifice 481 of gas port member 480). The first number (31%) corresponds to the gas concentration obtained with gas port member 480.

FIGS. 20B and 20C show the air entrainment window in partially open positions in which the window 560 formed in the shutter 550 is not in complete registration with the window 520 formed in the body 510. It will be appreciated that FIG. 20B shows a partially open air entrainment window.

It will be appreciated that the openness of the air entrainment window is very similar in size in FIG. 20B and in FIG. 20C; however, the two different resulting gas concentrations (e.g., 28% vs. 40%) is based on whether the gas port member 470 or gas port member 480 is used. When the larger sized gas port member 470 is used, a gas concentration of 40% is obtained when the window is in the position of FIG. 20C. Conversely, when the smaller sized gas port member 480 is used, a gas concentration of 28% is obtained when the air entrainment window is placed in the partially open position of FIG. 20B.

It will be appreciated that other partially open positions can be used with the present system.

It will also be understood that the gas entrainment valve member 500 can be used with other venturi members besides the multi-port venturi member 450 that is shown paired with the member 500 in the assembly of FIG. 8. For example, the venturi connector assembly of FIGS. 1-7 can be used with the gas entrainment valve member 500. In particular and similar to the system of FIG. 8, the combination of the venturi connector assembly of FIGS. 1-7 and with the gas entrainment valve member 500 provides two different air entrainment windows that are spaced apart from one another. More specifically, the combination provides two air entrainment windows that are located in series between the gas source and the patient interface (mask) 410. It will also be appreciated that the gas entrainment valve member 500 can be used with any traditional venturi (venturi connector) to provide a dual air entrainment window structure.

Unlike a conventional venturi design, the present invention teaches the use of two connector members that provide the dual window design (dual air entrainment windows) with one air entrainment window being located serially downstream from the other window and one window being adjustable in nature in that the degree of which the window is open can be adjusted by the user.

The invention is described in detail with reference to particular embodiments thereof, but the scope of the invention is to be gauged by the claims that follow and also by those modifications that provide equivalent features to those that are claimed as such modifications are still within the spirit and scope of the invention.

What is claimed is:

1. A venturi connector comprising:
   a housing having a mixing chamber defined therein and at least one window that is in fluid communication with the mixing chamber and is open to atmosphere to allow air to be entrained into the mixing chamber to form a venturi effect;
   a gas port extending outwardly from the housing for connecting to a supplemental gas source, the gas port defining a gas flow path for delivering the supplemental gas to the mixing chamber; and
   a nozzle actuator member comprising a body having a plurality of discrete nozzles formed therein, the nozzles being defined by different sized venturi orifices through which gas flows; the nozzle actuator member being disposed within one window formed in the housing between the gas port and the mixing chamber such that the position of the nozzle actuator member within the housing can be adjusted so as to position one of the discrete nozzles into the gas flow path, thereby controlling the flow rate of the supplemental gas into the mixing chamber and a concentration of the supplemental gas delivered to a patient;
   wherein the housing including a lower hub having a lower sealing surface and an upper hub having an upper sealing surface, the lower hub being defined at one end of the gas port, the lower and upper hubs defining the gas flow path with the upper hub forming a gas exit into the mixing chamber, the nozzle actuator member being rotatable within the housing to permit one select nozzle to be positioned between the lower and upper hubs and placed within the gas flow path;
   wherein the housing includes a first retention member that is connected to the lower hub and a second retention member that is connected to the upper hub, the nozzle actuator member having a first shaft section extending outwardly from a top face of the body of the nozzle actuator member and a second shaft section extending outwardly from a bottom face of the nozzle actuator member, the first shaft section being rotatably coupled to the second retention member and the second shaft section being rotatably coupled to the first retention member to permit rotation of the nozzle actuator member within the housing to allow one select nozzle to be positioned between the lower and upper hubs and placed within the gas flow path.

2. The connector of claim 1, wherein the first shaft section and the second retention member have complementary detents that engage one another and provide tactile feedback to a user as the nozzle actuator member is rotated within the housing.

3. The connector of claim 1, wherein the nozzle actuator member is snap-fittingly coupled to the housing.

4. The connector of claim 1, wherein the lower hub, upper hub and one select nozzle are centrally located within the housing.

5. The connector of claim 1, wherein the at least one window comprises two windows formed in the housing with the nozzle actuator member being at least partially disposed within one window of the two windows.

6. The connector of claim 1, wherein the nozzle actuator member is eccentrically coupled to the housing.

7. The connector of claim 1, wherein the nozzle actuator member includes six discrete nozzles that are spaced apart and formed circumferentially about a center axis about which the nozzle actuator member rotates within the housing.

8. The connector of claim 7, wherein the orifices of the six nozzles are configured to produce gas concentrations of 24%, 28%, 31%, 35%, 40% and 50%, respectively.

9. A venturi connector comprising:
a housing having a mixing chamber defined therein and at least one window that is in fluid communication with the mixing chamber and is open to atmosphere to allow air to be entrained into the mixing chamber to form a venturi effect;
a gas port extending outwardly from the housing for connecting to a supplemental gas source, the gas port defining a gas flow path for delivering the supplemental gas to the mixing chamber; and
a nozzle actuator member comprising a body having a plurality of discrete nozzles formed therein, the nozzles being defined by different sized venturi orifices through which gas flows; the nozzle actuator member being disposed within one window formed in the housing between the gas port and the mixing chamber such that the position of the nozzle actuator member within the housing can be adjusted so as to position one of the discrete nozzles into the gas flow path, thereby controlling the flow rate of the supplemental gas into the mixing chamber and a concentration of the supplemental gas delivered to a patient;
wherein the at least one window comprises two windows formed in the housing with the nozzle actuator member being at least partially disposed within one window of the two windows; wherein the body of the nozzle actuator member extends radially beyond an outer periphery of the housing.

10. A venturi connector comprising:
a housing having a mixing chamber defined therein and at least one window that is in fluid communication with the mixing chamber and is open to atmosphere to allow air to be entrained into the mixing chamber to form a venturi effect;
a gas port extending outwardly from the housing for connecting to a supplemental gas source, the gas port defining a gas flow path for delivering the supplemental gas to the mixing chamber; and
a nozzle actuator member comprising a body having a plurality of discrete nozzles formed therein, the nozzles being defined by different sized venturi orifices through which gas flows; the nozzle actuator member being disposed within one window formed in the housing between the gas port and the mixing chamber such that the position of the nozzle actuator member within the housing can be adjusted so as to position one of the discrete nozzles into the gas flow path, thereby controlling the flow rate of the supplemental gas into the mixing chamber and a concentration of the supplemental gas delivered to a patient; wherein the nozzle actuator member includes a peripheral wall on which discrete nozzle indicia are formed to indicate a gas concentration that is produced by a respective nozzle, each nozzle having associated nozzle indicia.

11. The connector of claim 10, wherein the nozzle indicia are circumferentially offset from the respective nozzle to which they relates.

12. The connector of claim 11, wherein the nozzle indicia are located about 180 degrees from the respective nozzle to which they relate.

13. A venturi nozzle member for use in a venturi connector housing comprising:
a body having a plurality of discrete venturi nozzles formed therein, the nozzles being defined by different sized venturi orifices through which supplemental gas flows, the body having means for rotatably coupling the body to the venturi connector housing;
wherein the means comprises a first shaft section extending upwardly from a top surface of the body and a second shaft section extending downwardly from a bottom surface of the body, the first and second shaft sections being axially aligned, the body rotating about the first and second shaft sections;
wherein the first shaft section includes detents for restricting free rotation of the body within the venturi connector housing.

14. The venturi nozzle member of claim 13, wherein there are six discrete nozzles that are spaced apart and formed circumferentially about a center axis about which the nozzle actuator member rotates within the housing.

15. The venturi nozzle member of claim 14, wherein the orifices of the six nozzles are configured to produce gas concentrations of 24%, 28%, 31%, 35%, 40% and 50%, respectively.

16. The venturi nozzle member of claim 13, wherein the body includes a peripheral wall on which discrete nozzle indicia are formed to indicate a gas concentration that is produced by a respective nozzle, each nozzle having associated nozzle indicia.

17. The venturi nozzle member of claim 16, wherein the nozzle indicia are circumferentially offset from the respective nozzle to which it relates they relate.

18. The venturi nozzle member of claim 17, wherein the nozzle indicia are located about 180 degrees from the respective nozzle to which they relate.

* * * * *